(12) United States Patent
Mezhinsky et al.

(10) Patent No.: US 7,193,169 B2
(45) Date of Patent: Mar. 20, 2007

(54) ERGONOMIC FOOTSWITCH

(75) Inventors: Victor B. Mezhinsky, Brea, CA (US); Steven T. Charles, Memphis, TN (US)

(73) Assignee: Alcon, Inc., Fort Worth, TX (US)

( * ) Notice: Subject to any disclaimer, the term of this patent is extended or adjusted under 35 U.S.C. 154(b) by 0 days.

(21) Appl. No.: 10/974,150

(22) Filed: Oct. 27, 2004

(65) Prior Publication Data

US 2005/0109595 A1    May 26, 2005

Related U.S. Application Data

(60) Provisional application No. 60/515,255, filed on Oct. 29, 2003.

(51) Int. Cl.
*H01H 29/16* (2006.01)

(52) U.S. Cl. ..................... 200/200; 200/86.5

(58) Field of Classification Search ............... 200/200, 200/86.5, 52 R; 606/1, 4, 170, 171; 74/560, 74/512; 307/119; D13/167; 84/422.1; 604/30; 318/685; 36/117.3; 398/113; 417/219; 377/2; 297/217.3

See application file for complete search history.

(56) References Cited

U.S. PATENT DOCUMENTS

| | | | |
|---|---|---|---|
| 4,172,217 A * | 10/1979 | Miller ...................... 200/86.5 |
| 4,267,414 A | 5/1981 | Brueggeman |
| 4,383,167 A | 5/1983 | Gmeinder et al. |
| 4,652,215 A | 3/1987 | Kuroyanagi et al. |
| 4,837,857 A | 6/1989 | Scheller et al. |
| 4,901,454 A | 2/1990 | Walkhoff |
| 4,965,417 A | 10/1990 | Massie |
| 4,983,901 A | 1/1991 | Lehmer |
| 5,091,656 A | 2/1992 | Gahn |
| 5,268,624 A | 12/1993 | Zanger |
| 5,423,231 A * | 6/1995 | Helfrich et al. ............... 74/561 |
| 5,535,642 A * | 7/1996 | Moll ........................... 74/561 |
| 5,554,894 A | 9/1996 | Sepielli |
| 5,580,347 A | 12/1996 | Reimels |
| 5,635,777 A * | 6/1997 | Telymonde et al. ......... 307/119 |
| 5,787,760 A | 8/1998 | Thorlakson |
| 5,983,749 A | 11/1999 | Holtorf |
| 5,990,400 A | 11/1999 | Hoshino |
| 6,010,496 A | 1/2000 | Appelbaum et al. |
| 6,150,623 A | 11/2000 | Chen |
| 6,179,829 B1 | 1/2001 | Bisch et al. |
| 6,360,630 B2 | 3/2002 | Holtorf |
| 6,452,120 B1 | 9/2002 | Chen |

(Continued)

FOREIGN PATENT DOCUMENTS

GB    1 063 067 A    3/1967

(Continued)

*Primary Examiner*—K. Lee
*Assistant Examiner*—Lheiren Mae A. Anglo
(74) *Attorney, Agent, or Firm*—Strasburger & Price LLP

(57) ABSTRACT

An ergonomic footswitch having a substantially planar tiltable treadle positioned on a base enables up and down or pitch movement of the footswitch around an axis of rotation located on the horizontal rotational axis of an operator's ankle. This arrangement reduces fatigue in the operator's leg and ankle and also permits the operator to vary the speed of an instrument or vary an operational parameter of the instrument via both the up and down motion of the treadle.

2 Claims, 2 Drawing Sheets

U.S. PATENT DOCUMENTS

| | | |
|---|---|---|
| 6,514,268 B2 | 2/2003 | Finlay et al. |
| 6,536,300 B1 * | 3/2003 | Gonring ................ 74/513 |
| D478,323 S | 8/2003 | Peterson et al. |
| 6,639,332 B2 | 10/2003 | Metzler et al. |
| 6,659,998 B2 | 12/2003 | DeHoogh et al. |
| 6,674,030 B2 | 1/2004 | Chen et al. |
| 6,743,245 B2 | 6/2004 | Lobdell |
| 6,784,388 B1 * | 8/2004 | Braaten ................ 200/86.5 |
| 2003/0047434 A1 | 3/2003 | Hanson et al. |
| 2003/0073980 A1 | 4/2003 | Finlay et al. |
| 2003/0213333 A1 | 11/2003 | McVicar |
| 2004/0106915 A1 | 6/2004 | Thoe |

FOREIGN PATENT DOCUMENTS

| | | |
|---|---|---|
| WO | WO 96/13845 | 5/1996 |
| WO | WO 98/08442 | 3/1998 |
| WO | WO 99/14648 | 3/1999 |
| WO | WO 00/12037 | 3/2000 |
| WO | WO 02/01310 | 1/2002 |
| WO | WO 03/053293 | 7/2003 |
| WO | WO 03/053294 | 7/2003 |

* cited by examiner

ERGONOMIC FOOTSWITCH

This application claims priority from Provisional U.S. Patent Application No. 60/515,255, filed Oct. 29, 2003.

FIELD OF INVENTION

This invention relates to footswitches; more particularly, the present invention relates to footswitches typically used to operate equipment associated with the treatment of a patient.

BACKGROUND

During the operation of complex equipment used to treat a patient; for example, in a delicate surgical procedure such as ophthalmic surgery, a surgeon, physician, dentist, or veterinarian may use a variety of pneumatic and electronically driven handpieces. The handpieces are operated by a variety of control systems. The control systems, in turn, receive inputs from a variety of different peripheral devices configured to receive manual control inputs.

One of the most important manually controlled peripheral devices is a footswitch. Exemplary footswitches are disclosed in a variety of U.S. patents, including U.S. Pat. No. 4,837,857 (Scheller, et al.), U.S. Pat. No. 4,965,417 (Massie), U.S. Pat. No. 4,983,901 (Lehmer), U.S. Pat. No. 5,091,656 (Gahn), U.S. Pat. No. 5,268,624 (Zanger), U.S. Pat. No. 5,554,894 (Sepielli), U.S. Pat. No. 5,580,347 (Reimels), U.S. Pat. No. 5,635,777 (Telymonde, et al.), U.S. Pat. No. 5,787,760 (Thorlakson), U.S. Pat. No. 5,983,749 (Holtorf), and U.S. Pat. No. 6,179,829 B1 (Bisch, et al.), and in International Patent Application Publications Nos. WO 98/08442 (Bisch, et al.), WO 00/12037 (Chen), and WO 02/01310 (Chen).

The aforementioned exemplary patents and patent applications focus primarily on the operability or functional attributes of footswitches—not on the ergonomic usability of a footswitch. Accordingly, it is not unusual for an operator of a prior art footswitch to experience foot and/or leg fatigue, particularly when performing repetitive motions over a long period of time. This foot and leg fatigue affects the ability of a physician, surgeon, dentist, or veterinarian to properly control motion inputs to the footswitch. In extreme circumstances, the result of operator fatigue may be inadvertent improper operation of a handpiece. Such improper operation could be injurious to the patient.

Therefore, a need remains in the art to provide a footswitch for use by a physician, surgeon, dentist, or veterinarian whose operation is ergonomically designed. Such ergonomic design will reduce foot and leg fatigue and thereby reduce the risk of inadvertent patient injury.

SUMMARY

The present invention provides a footswitch for use by physicians, surgeons, dentists, veterinarians, and the like. The disclosed footswitch is ergonomically designed for reducing foot and leg fatigue.

The disclosed footswitch allows for motion of the operator's leg and knee which is less fatiguing. This less fatiguing motion comes from co-locating the treadle axis of rotation with the substantially horizontal rotational axis of the operator's ankle. By co-locating the treadle axis of rotation with the substantially horizontal axis of the operator's ankle, the rotation of the operator's foot allows for both up and down control movements. Such up and down control movements may then be used to control the operation or motion of a variety of microsurgical instruments.

DRAWINGS

A better understanding of the ergonomic footswitch of the present invention and the following description of the embodiments may be held by reference to the drawings wherein.

DETAILED DESCRIPTION

Figure 1:
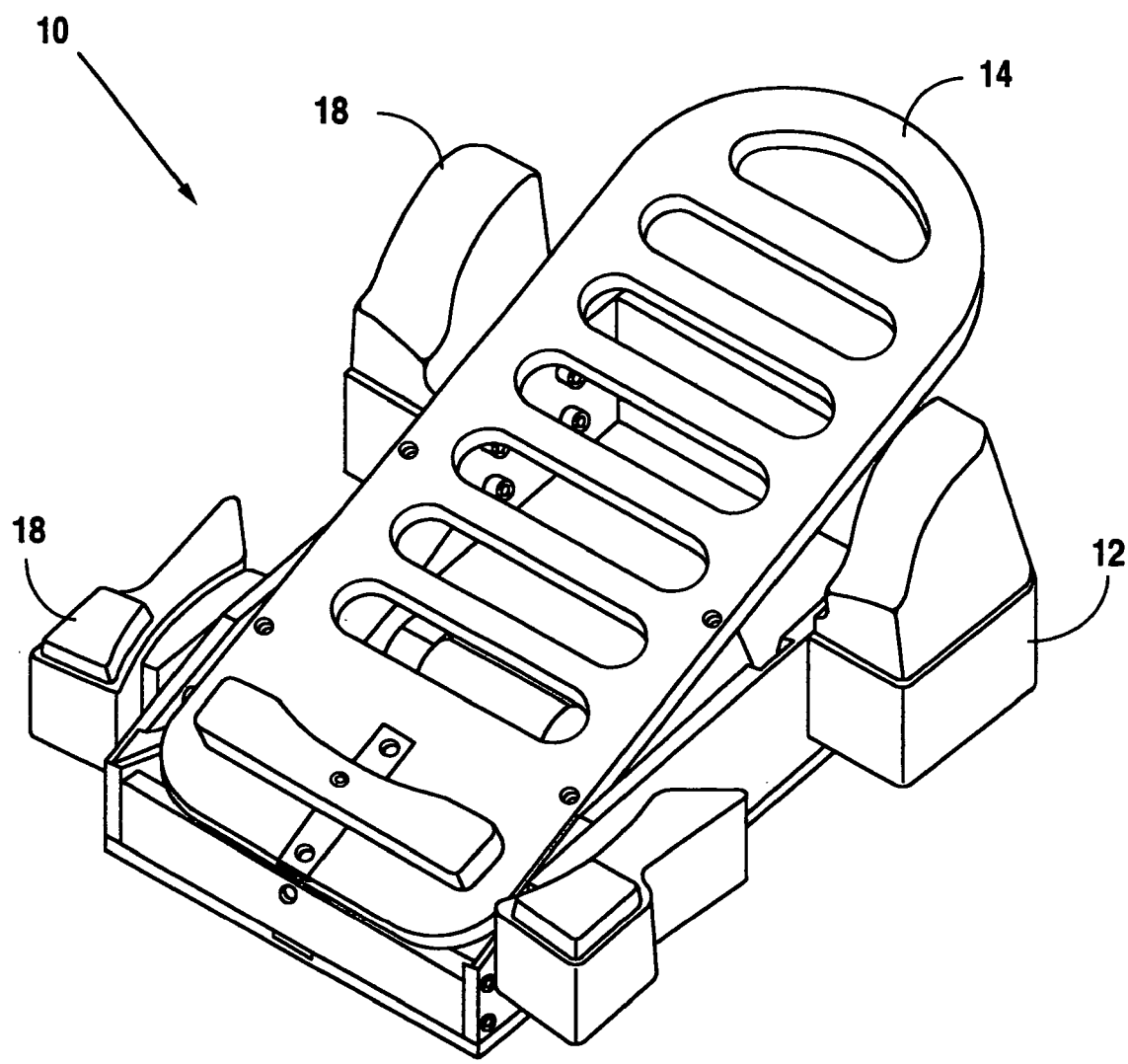
FIG. 1 is a perspective view of the footswitch of the present invention.

As best seen in the perspective view of the footswitch 10 shown in FIG. 1, the present invention generally includes a base portion 12, a substantially planar foot pedal or tiltable treadle 14, and side or wing switches 18. Commercially available footswitches are made from a variety of materials including stainless steel, titanium, and plastic.

Figure 2:
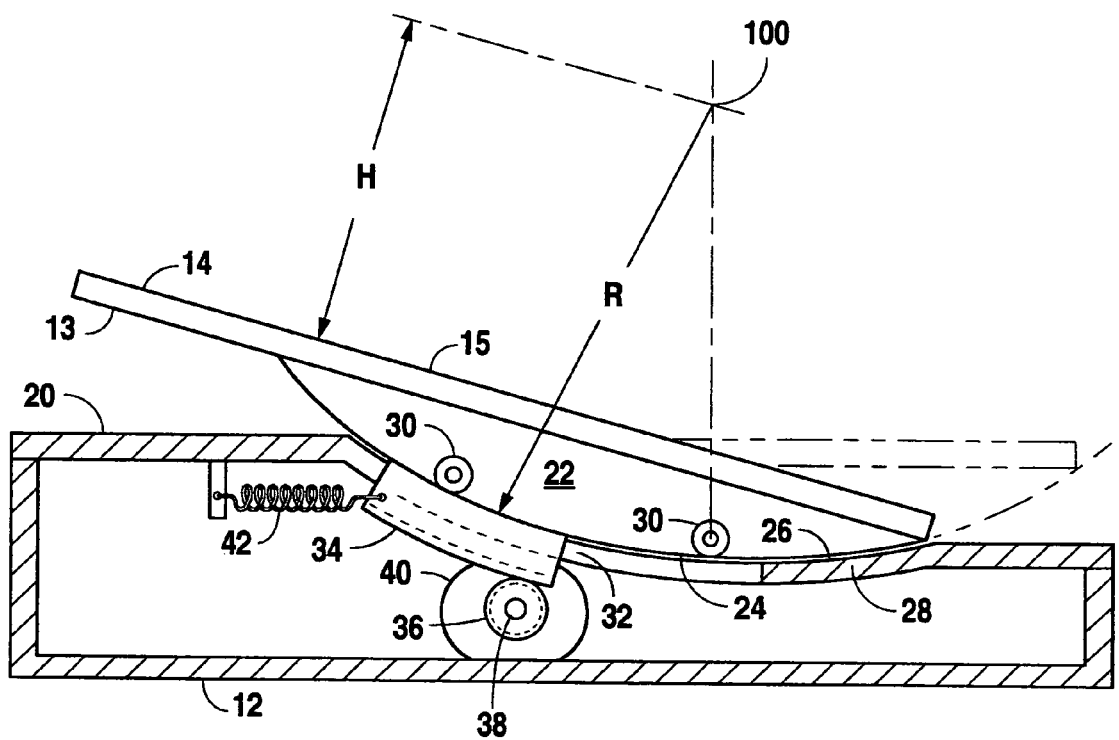
FIG. 2 is a side elevational schematic view of the footswitch in partial section showing the rocking motion of the foot pedal.

As best shown in FIG. 2, the motion control assembly 20 contained in the base portion 12 provides the ergonomic design which reduces the foot and leg fatigue of an operator. Specifically, the foot pedal or tiltable treadle 14 is substantially planar. The top side 15 of the foot pedal or tiltable treadle 14 is flat and is sized to engage the bottom of an operator's foot (not shown). The bottom side 13 of the foot pedal or tiltable treadle 14 includes an arcuate projection 22. In the illustrated embodiment, the perimeter 24 of arcuate projection 22 matches the contour 26 of an arcuate depression or arcuate slot 28 formed in the top of the base 12. The contour 26 of the arcuate depression 28 has a curvature with a radius R extending from an origin that is co-linear with the operator's ankle 100. The perimeter of the arcuate projection 22 needs not match the contour of the arcuate depression 28.

Friction forces between the perimeter 24 of the arcuate projection 22 and the contour 26 of the arcuate depression 28 may be reduced by the use of anti-friction roller bearings 30 which ride on the contour 26 of the arcuate depression 28 in the space between the arcuate projection 22 and the contour 26 of the arcuate depression 28. Those of ordinary skill in the art will understand that other anti-friction force systems may be used, such as a low-friction coating made from a low-friction material such as Teflon®.

In the illustrated embodiment, the arcuate depression 28 includes a longitudinal slot 32 formed therein. This longitudinal slot 32 provides an opening through which an arcuate gear sector 34 may pass. The arcuate gear sector 34 is positioned to engage a mating gear 36, such as a spur gear, affixed to a shaft 38 extending from a motor encoder or potentiometer 40. Thus, when the shaft 38 is caused to rotate in a clockwise direction by the interaction of the arcuate gear sector 34 with the mating gear 36, a first electrical signal is produced. When the shaft 38 is caused to rotate in a counter-clockwise direction, a second electrical signal is produced. The electrical signal produces a predetermined response in the handpiece being used by the operator. For example, the movement of the foot pedal or tiltable treadle 14 may control the speed of a drill motor in the hands of a dentist, the reciprocal action of a forceps or scissors mechanism, or the operation of a vitrectomy probe in the hands of an ophthalmic surgeon, or the intensity of a light source in the hands of a physician.

Optionally, a spring bias mechanism 42 may be used to provide mechanical feedback of the amount of deflection or pitch movement of the foot pedal or tiltable treadle 14 from a home or neutral position. Or the spring bias 42 may simply be used to return the foot pedal or tiltable treadle 14 to a home or neutral position when the procedure requiring the use of the footswitch 10 has been completed. While a mechanical spring 42 is shown in FIG. 2, those of ordinary skill in the art will understand that other types of bias may be used such as a fluidic or magnetic bias.

As may be best seen in FIG. 2, the foot pedal or tiltable treadle 14 is positioned on the base portion 12 so that the rotational or pitch movement of the tiltable treadle 14 is about the ankle axis 100 of the operator. In most prior art footswitches, the axis of rotation is positioned to be close to the center of the operator's foot.

Placement of the foot pedal or tiltable treadle 14 on the base 12 to enable movement about the substantially horizontal rotational axis of the operator's ankle 100 provides three advantages. First, foot and leg fatigue are reduced, as the operator's foot is caused to move about the ankle's natural axis of rotation. Second, the disclosed footswitch 10 may be used to provide a first input by applying pressure to change the pitch of the tiltable treadle 14 by moving the front of the foot pedal or tiltable treadle 14 down, and a second input by applying pressure to change the pitch of the tiltable treadle 14 by moving the rear of the foot pedal or tiltable treadle 14 down. Third, because the key geometric relationship is placement of the substantially horizontal rotational axis 100 of the operator's ankle over the low point of the foot pedal or tiltable treadle 14, there is no need for special adjustments to accommodate the length of or width of the operator's foot.

The simplicity of construction of the disclosed footswitch provides greater reliability. The low profile and footprint of the base 12 enables greater stability and rigidity as well as giving the disclosed footswitch a lower profile and smaller size.

In an alternative embodiment, the distance between the upper surface and the operator ankle axis can be made to be adjustable to customize the footswitch for those individuals who must use the disclosed footswitch for long periods of time. In yet another alternate embodiment, the distance between the ankle axis and the rear portion of the foot pedal or tiltable treadle 14 may be made to be adjustable to accommodate special-needs operators.

In the preferred embodiment, the contour 26 on the top of the arcuate depression 28 in the base 12 has a radius R from an origin which is co-linear from the operator's ankle 100. It is this radius R which determines the axis of rotation, together with height H. It has been found that a height H of approximately 5 inches will accommodate nearly all potential operators.

While the present system and method has been disclosed according to the preferred embodiment of the invention, those of ordinary skill in the art will understand that other embodiments have also been enabled. Such other embodiments shall fall within the scope and meaning of the appended claims.

We claim:

1. An ergonomic footswitch comprising:
    a spring biased substantially planar tiltable treadle;
    said spring biased substantially planar tiltable treadle including a top portion constructed and arranged for contact with the bottom of an operator's foot and a bottom portion including an arcuate projection;
    a base or means for supporting said spring biased substantially planar tiltable treadle, said base or means for supporting said spring biased substantially planar tiltable treadle including an arcuate depression constructed and arrange to conform to said arcuate projection;
    said arcuate depression further having a slot formed therein;
    said arcuate depression being located on said base or means for supporting said spring biased substantially planar tiltable treadle;
    a friction reduction roller constructed and arranged for rolling contact support between said spring biased substantially planar tiltable treadle and said base;
    said friction reduction roller being positioned on said arcuate projection to enable pitch movement of said spring biased substantially planar treadle about the ankle axis of the operator;
    an angular position sensor constructed and arranged for providing an electrical signal indicative of the position of said spring biased substantially planar tiltable treadle.

2. The ergonomic footswitch as defined in claim 1 wherein said angular position sensor senses movement of said spring biased substantially planar tiltable treadle in two directions.

* * * * *